United States Patent
Schatz

Patent Number: 6,055,843
Date of Patent: May 2, 2000

[54] METHOD FOR TESTING THE STABILITY OF INSTALLED WOODEN UTILITY POLES IN A NON-DESTRUCTIVE MANNER, IN PARTICULAR TO DETERMINE DECAY CAUSED BY FUNGAL GROWTH OR INSECT INFESTATION

[75] Inventor: Reinhard Schatz, Stuttgart, Germany

[73] Assignee: Deutsche Telekom AG, Bonn, Germany

[21] Appl. No.: 09/163,947

[22] Filed: Sep. 30, 1998

[30] Foreign Application Priority Data

Sep. 30, 1997 [DE] Germany ............... 197 43 119

[51] Int. Cl.⁷ ............... G01M 5/00; G01M 19/00; G01N 3/42

[52] U.S. Cl. ............... 73/12.01; 73/788; 73/865.8; 73/82

[58] Field of Search ............... 73/12.01, 12.09, 73/81, 82, 760, 788, 865.8

[56] References Cited

U.S. PATENT DOCUMENTS

| | | | |
|---|---|---|---|
| 3,879,982 | 4/1975 | Schmidt | 73/12.01 |
| 4,182,163 | 1/1980 | Hoffmeyer | 73/82 |
| 4,236,402 | 12/1980 | McGuire | 73/82 |
| 4,640,119 | 2/1987 | Ludwig | 73/12.09 |
| 5,672,809 | 9/1997 | Brandt | 73/12.01 |
| 5,841,019 | 11/1998 | Drabrin et al. | 73/12.09 |

*Primary Examiner*—Hezron Williams
*Assistant Examiner*—Chad Soliz
*Attorney, Agent, or Firm*—Kenyon & Kenyon

[57] ABSTRACT

A method for testing the stability of installed wooden utility poles in a non-destructive manner, in particular to determine decay caused by fungal growth or insect infestation. A quantity E' that is proportional to the modulus of elasticity E of the utility pole is measured above ground level at at least two different heights which are spaced apart by at least one meter, one height being directly at ground level, by shooting a pin with a defined energy at the utility pole and measuring its deflection when it springs back. The conditions of stability are fulfilled when the quantities E' measured at different heights deviate from one another by less than 30%. The invention enables one to objectively assess the condition of utility poles as well as to quantitatively characterize this condition.

6 Claims, 1 Drawing Sheet shoot a pin with a defined energy at the utility pole at at least a first height above ground level and a second height above ground level spaced apart by at least one meter — 102 measure at the first height and the second height a spring back deflection of the pin to determine a quantity E' at each height which is proportional to the modulus of elasticity E of the utility pole — 104 compare the quantity determined at the first height with the quantity determined at the second height — 106 shoot a pin with a defined energy at the utility pole at at least a first height above ground level and a second height above ground level spaced apart by at least one meter — 102 measure at the first height and the second height a spring back deflection of the pin to determine a quantity E' at each height which is proportional to the modulus of elasticity E of the utility pole — 104 compare the quantity determined at the first height with the quantity determined at the second height — 106

Fig. 1

METHOD FOR TESTING THE STABILITY OF INSTALLED WOODEN UTILITY POLES IN A NON-DESTRUCTIVE MANNER, IN PARTICULAR TO DETERMINE DECAY CAUSED BY FUNGAL GROWTH OR INSECT INFESTATION

FIELD OF THE INVENTION

The present invention relates generally to a method for testing the stability of installed wooden utility poles in a non-destructive manner, and, in particular, to a method for testing the stability of installed wooden utility poles in a non-destructive manner to determine decay caused by fungal growth or insect infestation.

RELATED TECHNOLOGY

Wooden utility poles installed in the ground are often used to support aerial lines, particularly within the framework of a telephone network and power supply lines. Wood is prone to loss of strength due to fungal growth or insect infestation. Therefore, occupational safety standards may stipulate that each pole be tested for stability before an ascent of the pole is made. Moreover, independently of any ascents, poles may be regularly tested for stability within the scope of traffic safety.

At the present time, stability tests are performed by knocking with a hammer, considerable experience in testing forces being required to assess the results. The tester makes a subjective assessment of the acoustical result, i.e., the noise, produced by knocking on the pole.

Another way to check the stability is to obtain a drilling core sample at ground level, i.e., directly in the area where the pole emerges from the ground. The ground-level area of the pole is most at risk because it is there that the wood comes in contact with air and the ground moisture. On the whole, therefore, the strength of the drilling core obtained there should provide information about the strength of the pole. Preparing and assessing drilling cores of this kind, however, requires extensive experience and practice. Since such extensive experience and practice are rare, and since considerable energy needs to be expended to uncover the ground level area, workers may forgo performing a stability test before climbing up the pole. Another drawback of spot drilling the pole is that it is a somewhat destructive process. Repeated stability tests which perforate the pole at ground level may eventually shorten the pole's service life.

Thus, the known methods for testing the condition—in particular, the stability—of utility poles are merely qualitative methods which assume a wealth of experience on the part of the tester in order to arrive at a test result. It is not possible at the present time to perform quantitative comparisons on the conditions of a plurality of utility poles, or even an entire line of poles.

SUMMARY OF THE INVENTION

An object of the present invention is to provide a method for testing the stability of installed wooden utility poles which is non-destructive, and which enables the stability to be evaluated without requiring extensive experience on the part of the tester.

The present invention provides a method for testing the stability of installed wooden utility poles in a non-destructive manner, in particular to determine decay caused by fungal growth or insect infestation. A quantity E' that is proportional to the modulus of elasticity E of the utility pole is measured above ground level at least two different heights h, which are spaced apart by at least one meter, by shooting a pin, or bolt, with a defined energy at the utility pole and measuring its deflection when it springs back, the conditions of stability being fulfilled when the quantities E' measured at different heights deviate from one another by less than 30%.

Thus, the condition of a utility pole is able to be easily determined quantitatively and objectively on the basis of a numerical value, or on the basis of the percentage difference between two values.

BRIEF DESCRIPTION OF THE DRAWING

The present invention is elucidated below with reference to the drawing, in which:

FIG. 1 is a flowchart of a method according to the present invention.

DETAILED DESCRIPTION

FIG. 1 shows a flowchart of a method according to the present invention. As shown in block 102, a pin with a defined energy is shot at a utility pole at least first and second heights above ground level. The heights are preferably spaced apart by at least one meter. The deflection of the pin when it springs back, or the spring back deflection, is measured at each height to determine a quantity E' at each height which is proportional to the modulus of elasticity E of the utility pole, as shown in block 104. Then the quantities E' determined at each height are compared, as shown in block 106.

The measurable quantity E' is preferably measured at ground level, i.e., in the area where the pole emerges from the ground, as well as at a height of one to two meters above that. The ground-level measurement is preferably performed directly at ground level, i.e., within about 5 cm of ground level. Since ground level is the area that is most at risk for a utility pole made of wood, the comparison of the quantity E' measured at the two heights provides excellent information about the current state of stability. The modulus of elasticity of the endangered area, i.e., at ground level, is compared to the modulus of elasticity of the intact pole area.

The modulus of elasticity E, or the quantity E' that is proportional thereto, is determined quickly, reliably, and in a non-destructive manner with the aid of a wood-rebound test hammer. Rebound test hammers work according to the principle of a captive pin apparatus: inside the apparatus, a spring is tensioned, which allows a firing pin to hit the material to be tested with a defined energy. The tougher this material is, the more vigorously the pin springs back, the deflection of the pin when it springs back being a measure of the modulus of elasticity and, thus, of the pole's strength.

The method of the present invention gives information about the strength of the part of the pole that is accessible from the outside, the so-called alburnum, or sapwood area. The method cannot be used to test the condition of the pole's core. However, this is not a significant limitation on the usefulness of the method, since, as known from mechanical science, when working with cylindrical bodies that are subject to bending stress, the greatest share of the load is borne by the outer annular region. The core region inside this outer annular region essentially absorbs only compressive forces. Typically, however, parasitic infestation or a decline in woody wood pulp due to fungal growth occurs from the outside toward the inside, i.e., from the alburnum to the core. Therefore, it is acceptable to infer the flexural strength and, thus, the stability of the pole from the assessment of the outer wood layer, i.e., the entire alburnum region.

The method of the present invention makes it possible to quantitatively characterize and document the condition of wooden utility poles. As an example, full strength, average strength, and reduced strength are diagnosed at 0 to 10, 10 to 20, and 20 to 30% differences, respectively, in the two measured values. Total fungal infestation is diagnosed at more than a 30% difference.

What is claimed is:

1. A method for testing the stability of an installed wooden utility pole in a non-destructive manner comprising determining a quantity that is proportional to the modulus of elasticity E of the utility pole by:

shooting a pin with a defined energy at the utility pole; and measuring a spring back deflection of the pin;

the determining being performed above ground level at at least a first height and a second height spaced apart by at least one meter, a condition of stability being fulfilled when the quantity determined at the first height differs by less than 30% from the quantity determined at the second height.

2. The method as recited in claim 1 wherein the first height is within about 5 cm of ground level.

3. The method as recited in claim 1 wherein the testing the stability is for the purpose of determining decay caused by fungal growth or insect infestation.

4. The method as recited in claim 1 wherein a wood-rebound test hammer is used for shooting the pin.

5. The method as recited in claim 4 wherein the first height is in an area where the pole emerges from the ground and the second height is from one to two meters above the area.

6. A method for testing the stability of an installed wooden utility pole in a non-destructive manner comprising:

determining a quantity that is proportional to the modulus of elasticity E of the utility pole by shooting a pin with a defined energy at the utility pole and measuring a spring back deflection of the pin, the determining being performed above ground level at at least a first height and a second height spaced apart by at least one meter; and comparing the quantity measured at the first height with the quantity measured at the second height, a condition of stability being fulfilled when the quantity measured at the first height differs by less than a predetermined percentage from the quantity measured at the second height.

* * * * *